United States Patent [19]
Ohta et al.

[11] Patent Number: 5,900,255
[45] Date of Patent: May 4, 1999

[54] MATERIAL FOR PREVENTION AND TREATMENT OF OSTEOPOROSIS

[75] Inventors: Atsutane Ohta; Toshio Takizawa; Takashi Adachi, all of Saitama, Japan

[73] Assignee: Meiji Seika Kaisha, Ltd., Tokyo, Japan

[21] Appl. No.: 08/954,744

[22] Filed: Oct. 20, 1997

Related U.S. Application Data

[63] Continuation of application No. 08/704,616, filed as application No. PCT/JP95/00413, Mar. 13, 1995, abandoned.

[30] Foreign Application Priority Data

Mar. 15, 1994 [JP] Japan ......................... 6-68987

[51] Int. Cl.⁶ .................. A61K 33/42; A61K 33/26; A61K 33/06; A61K 31/715

[52] U.S. Cl. .................. 424/602; 424/646; 424/682; 514/54

[58] Field of Search ................... 424/682, 686, 424/687, 602, 646, 647, 648; 514/54, 55, 56, 57, 58, 59, 60

[56] References Cited

U.S. PATENT DOCUMENTS

| | | | |
|---|---|---|---|
| 4,689,228 | 8/1987 | Rosenberg | 424/153 |
| 4,867,989 | 9/1989 | Silva et al. | 426/5 |
| 5,431,929 | 7/1995 | Yatka et al. | 426/3 |
| 5,476,844 | 12/1995 | Cooper | 514/55 |

FOREIGN PATENT DOCUMENTS

| | | | |
|---|---|---|---|
| 4-349868 | 12/1992 | Japan | A23L 1/30 |
| 4-360664 | 12/1992 | Japan | A23L 1/30 |
| 5-238940 | 9/1993 | Japan | A61K 33/26 |
| 5-316997 | 12/1993 | Japan | A23L 1/30 |
| 6-40922 | 2/1994 | Japan | A61K 31/70 |
| 6-205653 | 7/1994 | Japan | A23L 1/30 |
| 6-228181 | 8/1994 | Japan | C07H 7/033 |
| 7-67575 | 3/1995 | Japan | A23L 1/29 |
| 6-205654 | 7/1996 | Japan | A23L 1/30 |

OTHER PUBLICATIONS

Ota Atsutane, et al., Journal of Japanese Society of Nutrition and Food Science, vol. 46, No. 2, pp. 123–129 (abstract only), 1993.

*Primary Examiner*—Raymond Henley, III
*Attorney, Agent, or Firm*—Sughrue, Mion, Zinn, Macpeak & Seas, PLLC

[57] ABSTRACT

A material for the prevention and treatment of osteoporosis characterized by containing minerals and indigestible oligosaccharides. The material for the prevention and treatment of osteoporosis according to the present invention is excellent in the absorption of calcium and the reduction in a bone salt amount which is observed in the osteoporosis can be depressed. Accordingly, by taking the material for the prevention and treatment of osteoporosis according to the present invention, the osteoporosis which often occurs particularly in postmenopausal women is effectively prevented and its progress can be retarded.

20 Claims, No Drawings

MATERIAL FOR PREVENTION AND TREATMENT OF OSTEOPOROSIS

This is a continuation of application Ser. No. 08/704,616 filed Sep. 12, 1996, now abandoned, which is a 371 of PCT/JP95/00413 filed Mar. 13, 1995.

TECHNICAL FIELD

This invention relates to a material for the prevention and treatment of osteoporosis which is excellent in absorbability of calcium and is capable of suppressing the reduction of a bone-salt amount and a bone density observed in the osteoporosis.

TECHNICAL BACKGROUND

Recently, various geriatric diseases have been increased with coming of an era of the advanced age society and now become to be a serious social problem. A typical example of these diseases is osteoporosis which is often observed in persons of advanced age, in particular, postmenopausal women. In bones, salts of calcium as well as phosphorus, magnesium and sodium are present in large amounts. In a recent national nutritional investigation, insufficient intake of calcium was pointed out, and this is assumed to be one of reasons for the increase of osteoporosis. From such a background, a number of calcium-enriched foods has been developed and is now commercially available. Further, an effect of the calcium replenishment on the therapy or the suppression of symptom of osteoporosis has been extensively studied.

However, there are not a few reports in which a mere replenishment of calcium is confirmed to be ineffective to the treatment or the suppression of symptom. The reason therefor is considered that, in persons of advanced age, it is highly possible that an absorption of calcium decreases, and that not only calcium but also minerals which constitute the bone are required to be adsorbed in a well-balanced manner.

The present inventors have already observed that indigestible oligosaccharides promote an absorption of minerals such as calcium, magnesium, phosphorus and iron, and, by taking an advantage of this activity, developed a magnesium replenishment (Japanese Patent Application No. Hei-5-191591) and an improving material for iron deficiency anemia (Japanese Patent Application No. Hei-5-313948) and filed patent applications therefor. Also, with respect to calcium, the present inventors observed that the indigestible oligosaccharides increase an absorption of calcium and further increase a calcium content in bones in the test using rats at a growth stage (Nippon Eiyo Shokuryo Gakkai-shi, 1993, Vol. 46, No. 2, pp 123–129), but their clinical significance was not apparent.

DISCLOSURE OF THE INVENTION

An object of the present invention is to provide a material for the prevention and treatment of osteoporosis which is not only excellent in absorbability of calcium but also capable of suppressing the reduction of the bone-salt amount and the bone density associated with the onset and progress of the osteoporosis.

As described above, the present inventors found that the intake of indigestible oligosaccharides increase an absorption of calcium in rats at a growth stage and further increases a calcium content in bones.

However, an affect of the indigestible oligosaccharides on a bone-salt amount in osteoporosis has not been observed.

The present inventors investigated the affect of the indigestible oligosaccharides on the bone-salt using osteoporosis model rats and confirmed that the intake of the indigestible oligosaccharides has a significant depressive effect on reduction in the bone-salt amount and the bone density of the osteoporosis model rats, and completed the present invention.

More specifically, the present invention provides a material for the prevention and treatment of osteoporosis characterized by containing minerals and indigestible oligosaccharides.

The material for the prevention and treatment of osteoporosis according to the present invention contains, as minerals, at least calcium among calcium, magnesium, phosphorus and iron which are main minerals of bones, and in particular, calcium plus magnesium and/or phosphorus (that is, it contains calcium and magnesium; calcium and phosphorus; or calcium, magnesium and phosphorus) are preferable.

As the minerals used in the present invention, for example, natural substances which contain calcium, magnesium and phosphorus in a well-balanced state such as a beef bone and a fish bone is preferably used, or calcium phosphate as a food additive which contains such calcium, magnesium and phosphorus in a well-balance state can be used. Also, natural substances such as egg shells, sea shells and oyster shells which mainly contain calcium can be used, or calcium carbonate, calcium chloride, calcium lactate, calcium gluconate and calcium citrate as food additives which mainly contain calcium can also be used.

The indigestible oligosaccharides used in the present invention are those which are not digested with digestive enzymes of the human, and specific examples thereof include fructo-oligosaccharides, raffinose, galacto-oligosaccharides, xylo-oligosaccharides, beet sugar and soybean oligosaccharides. In particular, fructo-oligosaccharides, raffinose, galacto-oligosaccharides and xylo-oligosaccharides are preferred. Oligosaccharides which are relatively highly digestive such as isomaltose are not suitable.

In the material for the prevention and treatment of osteoporosis according to the present invention, a ratio of calcium and the indigestible oligosaccharides is preferably from 1:1 to 1:20 (a weight ratio), and the ratio of calcium and the indigestible oligosaccharides of from 1:5 to 1:10 (a weight ratio) is particularly preferred.

When the ratio of calcium and the indigestible oligosaccharides is below 1:1 (a weight ratio), the desired effect cannot be expected. On the other hand, when the ratio exceeds 1:20 (a weight ratio), the intake of the indigestible oligosaccharides may possibly be an excess amount. Either of them is not preferred.

The material for the prevention and treatment of osteoporosis according to the present invention can be in any form such as a granular form, a capsule form, a tablet form, a powder form and a liquid form, and can be eaten as it is. However, needless to say, may be taken after having been formulated into other foods, condiments and food additives. Although a proportion in the case of formulating the material into other foods is not specifically limited, intake of the indigestible oligosaccharides in an excess amount may cause loose bowels depending upon the constitution and the physical condition. When the indigestible oligosaccharides are formulated in such a manner that the intake amount thereof is approximately 10 g per day, an effect for improving intestinal function can be also be expected.

BEST MODE FOR WORKING THE INVENTION

The present invention is further illustrated by the following Examples, but the present invention is not limited by these examples. Unless otherwise indicated, % is by weight.

EXAMPLE 1

The evaluation of the effect for preventing and treating the osteoporosis of the material for the prevention and treatment of osteoporosis according to the present invention was conducted by the method using ovary-extracted female rats which are ordinary used. (Literature references: Nippon Eiyo Shokuryo Gakkai-shi, 1990, Vol. 43, No. 6, pp437–443).

More specifically, 48 individuals of 18-week old SD type female rats were divided into 6 groups of 8 individuals per group. One group was sacrificed, and the femur were enucleated therefrom and presented to the measurement of bone-salt amount and bone density prior to the ovariectomy. With respect to the remaining 5 groups, the ovaries of both sides were removed from the back side under ether anesthesia to prepare the osteoporosis model rats by the removal of ovaries (hereinafter, referred to OVX rat), and the effect for the prevention and treatment of osteoporosis were evaluated in the following manner.

That is, one group of the OVX rat received a feed which did not contain the material for the prevention and treatment of osteoporosis according to the present invention for 4 weeks (a control group). On the other hand, the remaining four groups of the OVX rat received a feed containing the material for the prevention and treatment of osteoporosis according to the present invention for 4 weeks (groups receiving the material for the prevention and treatment of osteoporosis).

In the groups receiving the material for the prevention and treatment of osteoporosis, four types of feed which were different in the kind or ratio of the minerals and the indigestible oligosaccharides as shown in Table 1 were used.

In the compositions of these four types of feed, the compositions were prepared in similar formulations except that the increment of the material for the prevention and treatment of osteoporosis according to the present invention in the compositions was adjusted by deducting the amount of granulated sugar used. In group A, a composition of fructo-oligosaccharides mixed with beef bone meal (a calcium content=30%) at a proportion of 1.5:1 (by weight) was used; in group B, a composition of fructo-oligosaccharides mixed with beef bone meal (a calcium content=30%) at a proportion of 3:1 (by weight) was used; in group C, a composition of raffinose mixed with beef bone meal (a calcium content=30%) at a proportion of 3:1 (by weight) was used; and, in group D, a composition of galacto-oligosaccharides mixed with beef bone meal (a calcium content=30%) at a proportion of 3:1 (by weight) was used.

Four weeks after starting the feeding, the OVX rats were sacrificed, and the femur were enucleated. After removing soft tissues, the bone-salt amount and the bone density of the enucleated bones were measured using a double X-ray analyser (a product of Aroka Co., Ltd., DCS-600A). The femur was measured after equally dividing the whole femur into three parts, i.e., a part of the hip joint side, a part of the diaphysis, and a part of the knee joint side.

As shown in Table 2, the results indicated that, with respect to the femur of the OVX rat receiving the control feed (a control group), remarkable reductions in the bone-salt amount and the bone density were observed in the part of knee joint side as compared with the values measured prior to the ovariectomy. On the other hand, in the OVX rats receiving the materials for the prevention and treatment of osteoporosis B, C and D according to the present invention (the groups B, C and D receiving the material for the prevention and treatment of osteoporosis according to the present invention), the values of the bone-salt amount and the bone density in the part of hip joint side and the part of knee joint side were significantly high (P<0.05) as compared to those of the OVX rat receiving the control feed (a control group). Further, in the OVX rat receiving the material for the prevention and treatment of osteoporosis A (the group A receiving the material for the prevention and treatment of osteoporosis according to the present invention), the values of the bone-salt amount in the part of hip joint side, and the bone-salt amount and the bone density in the part of knee joint side were significantly high (P<0.05) as compared to those of the OVX rat receiving the control feed (the control group). Since fracture of hip joint is often observed in the osteoporosis, a significantly high bone-salt amount in the part of hip joint side has an important significance.

From the above results, it was confirmed that the intake of the material according to the present invention is effective for the prevention and the treatment of the osteoporosis.

TABLE 1

Composition of Test Feed

|  | Control | \multicolumn{4}{c}{Feed Containing Material for Prevention and Treatment of Osteoporosis of Present Invention} |
| --- | --- | --- | --- | --- | --- |
|  |  | A | B | C | D |
| Casein | 25.0 | 25.0 | 25.0 | 25.0 | 25.0 |
| Corn Starch | 56.7 | 56.7 | 56.7 | 56.7 | 56.7 |
| Granulated Sugar | 10.0 | 6.8 | 4.3 | 4.3 | 4.3 |
| Corn Oil | 5.0 | 5.0 | 5.0 | 5.0 | 5.0 |
| Vitamin Mixture (AIN-76 Modification) | 1.0 | 1.0 | 1.0 | 1.0 | 1.0 |
| Mineral Mixture *1 (Ca and P non-addition, AIN-76 Modification) | 1.26 | 1.26 | 1.26 | 1.26 | 1.26 |
| Beef Bone Meal Material for Prevention and Treatment of Osteoporosis of Present Invention | 1.0 | — | — | — | — |
| A *2 | — | 4.2 | — | — | — |
| B *3 | — | — | 6.7 | — | — |
| C *4 | — | — | — | 6.7 | — |
| D *5 | — | — | — | — | 6.7 |
| Calcium: Indigestible Oligosaccharides (a weight ratio) | — | 1:5 | 1:10 | 1:10 | 1:10 |

[Footnote of Table 1]
*1: Mineral Mixture (Ca and P are not added), contents in 1.26 g (unit of mg): MgO 800, NaCl 2590, $K_3C_6H_5O_7 \cdot H_2O$ 7700, $K_2SO_4$ 1820, $MnCO_3$ 123, iron citrate 210, $ZnCO_3$ 56, $CuCO_3$ 10.5, $Na_2SeO_3 \cdot 5H_2O$ 0.35, $KIO_3$ 0.35, and $Cr(SO_4)_2 \cdot 12H_2O$ 19.3
*2: A mixture of beef bone meal:powder of fructooligosaccharides (a trademark: Meioligo P; purity of oligosaccharides, 95% or more; a product of Meiji Seika Kaisha, Ltd.) = 1:1.5 (a weight ratio)
*3: A mixture of beef bone meal:powder of fructooligosaccharides (a trademark: Meioligo P; purity of oligosaccharides, 95% or more; a product of Meiji Seika Kaisha, Ltd.) = 1:3 (a weight ratio)
*4: A mixture of beef bone meal:raffinose (a reagent of special grade) = 1:3 (a weight ratio)
*5: A mixture of beef bone meal:powder of galactooligosaccharides (a trademark: Cup-oligo P; purity of oligosaccharides; 95% or more; a product of Nisshin Sugar Manufacturing Co., Ltd.) = 1:3 (a weight ratio)

TABLE 2

Amount of Bone-salt and Bone Density in Femur of Osteoporosis Model Rats

|  | Hip Joint Side | | Diaphysis | | Knee Joint Side | |
|---|---|---|---|---|---|---|
|  | Amount of Bone-salt (mg) | Bone Density (mg/cm$^2$) | Amount of Bone-salt (mg) | Bone Density (mg/cm$^2$) | Amount of Bone-salt (mg) | Bone Density (mg/cm$^2$) |
| Prior to Ovariectomy | 95 ± 6 | 158 ± 5 | 74 ± 5* | 139 ± 6 | 112 ± 8* | 181 ± 5* |
| Control | 95 ± 12 | 155 ± 6 | 81 ± 6 | 144 ± 3 | 92 ± 8 | 151 ± 7 |
| Groups receiving material for prevention and treatment of osteoporosis of present invention | | | | | | |
| A | 104 ± 7* | 159 ± 8 | 79 ± 4 | 143 ± 4 | 105 ± 9* | 162 ± 9* |
| B | 104 ± 4* | 163 ± 6* | 85 ± 6 | 146 ± 7 | 104 ± 8* | 160 ± 9* |
| C | 103 ± 3* | 162 ± 5* | 83 ± 5 | 144 ± 4 | 104 ± 7* | 161 ± 5* |
| D | 103 ± 5* | 162 ± 4* | 82 ± 7 | 144 ± 7 | 103 ± 6* | 159 ± 7* |

*A significant difference at a level of significance of 5% or less as compared with the control.

EXAMPLE 2

Biscuits were prepared using 5 parts by weight of the material for the prevention and treatment of osteoporosis according to the present invention obtained by mixing a beef bone meal (a calcium content, 30%) and fructo-oligosaccharides at a ratio of 1:6 (by weight) according the conventional procedure at the following formulation:

| | |
|---|---|
| Wheat Flour | 100 parts by weight |
| Sugar | 40 parts by weight |
| Material for prevention and treatment of osteoporosis of present invention | 5 parts by weight |
| Shortening | 20 parts by weight |
| Butter | 5 parts by weight |
| Egg yolk | 20 parts by weight |
| Salt | 1 parts by weight |
| Baking powder | 0.5 parts by weight |

The resulting product had a good baked color and a good swelling state and, as a resulting sampling, was comparable to a commercially available product.

EXAMPLE 3

Chocolates were prepared using 2 parts by weight of the material for the prevention and treatment of osteoporosis according to the present invention obtained by mixing a beef bone meal (a calcium content, 30%) and fructo-oligosaccharides at a ratio of 1:1.5 (by weight) according the conventional procedure in the following formulation:

| | |
|---|---|
| Cacao Mass | 20 parts by weight |
| Cacao Butter | 20 parts by weight |
| Material for prevention and treatment of osteoporosis of present invention | 2 parts by weight |
| Sugar | 40 parts by weight |
| Powdered Milk | 18 parts by weight |

As a result of sampling of the resulting product, it had a mild taste, a good melting in mouth and was a chocolate comparable to commercially available product.

EXAMPLE 4

Tablet candies were prepared using 10 parts by weight of the material for the prevention and treatment of osteoporosis according to the present invention obtained by mixing a beef bone meal (a calcium content, 30%) and fructo-oligosaccharides at a ratio of 1:0.3 (by weight) according the conventional procedure at the following formulation:

| | |
|---|---|
| Crystalline Glucose | 400 parts by weight |
| Material for prevention and treatment of osteoporosis of present invention | 10 parts by weight |
| Ascorbic Acid | 5 parts by weight |
| Citric Acid | 7 parts by weight |
| Sodium Caseinate | 7 parts by weight |
| Hardened Oil | 3 parts by weight |

As a result of sampling of the resulting product, it did not give a rough feeling and was a tablet candy comparable to a commercially available product.

INDUSTRIAL APPLICABILITY

The material for the prevention and treatment of osteoporosis according to the present invention is excellent in the absorption of calcium and the decrease in a bone salt amount which is observed in the osteoporosis can be depressed.

Accordingly, by taking the material for the prevention and treatment of osteoporosis according to the present invention, the osteoporosis which occurs particularly in postmenopausal women is effectively prevented and its progress can be retarded.

We claim:

1. A method for the prevention of osteoporosis which comprises administering to a person in need of treatment an effective amount of a material containing minerals and fructo-oligosaccharides.

2. The method as claimed in claim 1, wherein said minerals contain at least calcium and optionally at least one member selected from the group consisting of magnesium, phosphorous and iron.

3. The method as claimed in claim 1, wherein said minerals contain (A) calcium, magnesium and phosphorous, (B) calcium and magnesium, or (C) calcium and phosphorous.

4. The method as claimed in claim 1, wherein said minerals comprise calcium and a weight ratio of said calcium in said minerals to said fructo-oligosaccharides is from 1:1 to 1:20.

5. The method as claimed in claim 1, wherein said minerals comprise calcium and a weight ratio of said calcium in said minerals to said fructo-oligosaccharides is from 1:5 to 1:10.

6. The method as claimed in claim 1, wherein said person in need of treatment is a human female of an advanced age.

7. A method of preventing osteoporosis which comprises administering to a person in need of treatment a material containing (1) minerals containing at least calcium among calcium, magnesium, phosphorous and iron, and (2) fructo-oligosaccharides, wherein a weight ratio of calcium in said minerals to said fructo-oligosaccharides is from 1:1 to 1:20.

8. The method as claimed in claim 7, wherein said minerals contain (A) calcium, magnesium and phosphorous, (B) calcium and magnesium, or (C) calcium and phosphorous.

9. The method as claimed in claim 7, wherein a weight ratio of calcium in said minerals to said fructo-oligosaccharides is from 1:5 to 1:10.

10. The method as claimed in claim 7, wherein said person in need of treatment is a human female of an advanced age.

11. A method for the treatment of osteoporosis which comprises administering to a person in need of treatment an effective amount of a material containing minerals and fructo-oligosaccharides.

12. The method as claimed in claim 11, wherein said minerals contain at least calcium and optionally at least one member selected from the group consisting of magnesium, phosphorous and iron.

13. The method as claimed in claim 11, wherein said minerals contain (A) calcium, magnesium and phosphorous, (B) calcium and magnesium, or (C) calcium and phosphorous.

14. The method as claimed in claim 11, wherein said minerals comprise calcium and a weight ratio of said calcium in said minerals to said fructo-oligosaccharides is from 1:1 to 1:20.

15. The method as claimed in claim 11, wherein said minerals comprise calcium and a weight ratio of said calcium in said minerals to said fructo-oligosaccharides is from 1:5 to 1:10.

16. The method as claimed in claim 11, wherein said person in need of treatment is a human female of an advanced age.

17. A method of treating osteoporosis which comprises administering to a person in need of treatment a material containing (1) minerals containing at least calcium among calcium, magnesium, phosphorous and iron, and (2) fructo-oligosaccharides, wherein a weight ratio of calcium in said minerals to said fructo-oligosaccharides is from 1:1 to 1:20.

18. The method as claimed in claim 17, wherein said minerals contain (A) calcium, magnesium and phosphorous, (B) calcium and magnesium, or (C) calcium and phosphorous.

19. The method as claimed in claim 17, wherein a weight ratio of calcium in said minerals to said fructo-oligosaccharides is from 1:5 to 1:10.

20. The method as claimed in claim 17, wherein said person in need of treatment is a human female of an advanced age.

* * * * *